(12) United States Patent
Moro et al.

(10) Patent No.: US 8,524,260 B2
(45) Date of Patent: *Sep. 3, 2013

(54) METHOD FOR ENCAPSULATING OILS IN AN AQUEOUS MEDIUM WITH HASE POLYMER EMULSIONS, PRODUCTS OBTAINED, AND USES THEREOF

(75) Inventors: Jean Moro, Saint Didier de Formans (FR); David Platel, Saint-Maurice de Gourdans (FR); Jean-Marc Suau, Lucenay (FR); Olivier Guerret, La Tour de Salvagny (FR)

(73) Assignee: Coatex S.A.S., Genay (FR)

( * ) Notice: Subject to any disclaimer, the term of this patent is extended or adjusted under 35 U.S.C. 154(b) by 250 days.

This patent is subject to a terminal disclaimer.

(21) Appl. No.: 12/747,651

(22) PCT Filed: Dec. 3, 2008

(86) PCT No.: PCT/IB2008/003393
§ 371 (c)(1),
(2), (4) Date: Jun. 11, 2010

(87) PCT Pub. No.: WO2009/090462
PCT Pub. Date: Jul. 23, 2009

(65) Prior Publication Data
US 2010/0267564 A1 Oct. 21, 2010

(30) Foreign Application Priority Data

Dec. 20, 2007 (FR) ..................................... 07 08888

(51) Int. Cl.
| | | |
|---|---|---|
| A61K 8/02 | (2006.01) | |
| A61K 9/14 | (2006.01) | |
| A61K 31/59 | (2006.01) | |
| C08F 2/16 | (2006.01) | |
| C08G 8/10 | (2006.01) | |
| C08G 73/10 | (2006.01) | |
| C09D 11/02 | (2006.01) | |
| C08L 75/00 | (2006.01) | |

(52) U.S. Cl.
USPC ........... 424/401; 424/489; 424/490; 424/497; 424/498; 424/555; 510/418; 510/434; 524/800; 524/801; 524/804; 524/841; 524/313; 504/313; 504/320; 504/357; 504/359; 504/360; 523/1; 523/102; 523/105; 523/200; 523/335; 526/72; 526/89; 526/216; 526/348.3; 44/502; 44/397; 426/602; 426/609; 508/472; 516/133; 71/27

(58) Field of Classification Search
USPC ......... 504/313, 320, 357, 359, 360; 424/401, 424/489, 490, 497, 498; 523/1, 102, 105, 523/200, 202, 210, 211, 215, 334, 335; 524/800, 801, 804, 841, 845, 313; 526/72, 526/88, 89, 207, 213, 216, 348.2, 348.3; 44/502, 397; 426/602, 609; 508/472; 510/418, 510/434; 516/133; 71/27

See application file for complete search history.

(56) References Cited

U.S. PATENT DOCUMENTS

| | | |
|---|---|---|
| 4,421,902 A | 12/1983 | Chang et al. |
| 6,140,435 A | 10/2000 | Zanotti-Russo |
| 6,849,591 B1 * | 2/2005 | Boeckh et al. ................. 510/475 |
| 2002/0042448 A1 | 4/2002 | Sorrentino et al. |
| 2003/0068350 A1 | 4/2003 | Sorrentino et al. |
| 2003/0147825 A1 * | 8/2003 | Chiarelli et al. ........... 424/70.11 |
| 2003/0207988 A1 | 11/2003 | Tamareselvy et al. |
| 2007/0197704 A1 | 8/2007 | Walter et al. |
| 2008/0045646 A1 * | 2/2008 | Tamareselvy et al. ........ 524/555 |
| 2008/0103248 A1 | 5/2008 | Suau et al. |

FOREIGN PATENT DOCUMENTS

| | | |
|---|---|---|
| EP | 0 870 785 | 10/1998 |
| EP | 1 726 331 | 11/2006 |
| WO | 02 100374 | 12/2002 |
| WO | 03 062288 | 7/2003 |
| WO | 2006 016035 | 2/2006 |
| WO | 2007 101059 | 9/2007 |

* cited by examiner

*Primary Examiner* — Jane C Oswecki
(74) *Attorney, Agent, or Firm* — Oblon, Spivak, McClelland, Maier & Neustadt, L.L.P.

(57) ABSTRACT

The invention consists of a method for manufacturing an aqueous formulation containing at least one oil, and comprising the steps of mixing at least one associative polymer, one oil, and water, encapsulating the oil by increasing the pH to a value greater than 8, potentially precipitating the mixture by reducing the pH to a value less than 6, and potentially isolating the resulting particles by removing the water. The aqueous formulations, as with the aqueous dispersions, and the resulting solid particles constitute other objects of the invention.

16 Claims, No Drawings

METHOD FOR ENCAPSULATING OILS IN AN AQUEOUS MEDIUM WITH HASE POLYMER EMULSIONS, PRODUCTS OBTAINED, AND USES THEREOF

This application is a 371 of PCT/IB2008/003393 filed Dec. 3, 2008.

Oil is a generic term that designates fats which do not mix with water. Oils are fatty liquids, viscous, or even solid, and are of animal, vegetable, mineral, or synthetic origin. They include:
- vegetable and animal oils known as food oils, made up of lipids, and most often obtained by pressing;
- so-called "essential" vegetable oils which correspond to concentrated and hydrophobic liquids of volatile aromatic compounds from a plant (mixtures of various molecules, including terpenes such as non-aromatic carbon hydrates and alcohol-, aldehyde-, or cetone-based oxygenated compounds) obtained by distillation or chemical extraction using solvents;
- mineral oils, which are mixtures of hydrocarbons, obtained using refining;
- synthetic oils obtained through chemical synthesis of molecules, or hydro cracking mineral oils, and made up of highly varied molecules, which are carbon-based, silicon-based, fluoride-based, etc.

The oils are sometimes implemented in applications in which the water is considered a pollutant or a poison, but they are also employed in formulations that contain an aqueous phase, and some of these formulations are even sometimes mostly made up of water. These aqueous formulations which implement oils of diverse natures are, for example, cosmetic formulations, paints, hydraulic binders, fuels, lubricants, anti-foaming agents, cutting oils and quenching oils for metallurgy, fertilizers, and pharmaceutical, agrochemical, phytosanitary, detergent, and food oils, or formulations in the leather crafting industry, or coating industry.

Initially, various solutions were developed with a view to incorporating oils in aqueous formulations while trying to limit undesirable phenomena (demixing, phase separation, instability) which are inherent in the presence of an oil phase which is not or is barely dispersed in water. Such phenomena are all the more undesirable for the formulation in question from an aesthetic viewpoint (the overall appearance of the phase), rheologically (such as by altering the flow properties, related to the presence of an oil phase which is not dispersed in water), or with regard to its application performance (the uneven nature of the formulation, related to the poor condition of the oil dispersion, may lead to a degradation in its ultimate performance). These solutions particularly rely on the use of solvents or mixtures of surface active agents, whose function is to stabilize the oil phase in the water.

In addition to the increasingly restrictive legislation regarding the use of solvents and surface active agents, the development of a more recent technology has offered the person skilled in the art new opportunities for producing aqueous formulations containing oils: encapsulation technology. This technique makes it possible to chemically or physically isolate an oil from the aqueous phase in which it is incorporated: thus, any phenomena of instability are avoided, and the drawbacks mentioned above are remedied. Presently, two major encapsulation techniques are known: implementation of β-cyclodextrins, and encapsulation using organic polymers.

The first category uses β-cyclodextrins, which are natural molecules obtained by the enzymatic degradation of starch. They appear in the form of cyclical oligomers of glucose, and are characterized by the presence of a recess which enables them to "accommodate a host molecule", so as to form an inclusion complex. To that end, the document JP 2001 354515 describes the encapsulation of an oil in a micronized form using cyclodextrin, for cosmetic usage.

The second category is based on methods which implement organic polymers. Among these polymers, there are coacervation methods, which rely on coating an oil emulsion with a film of precipitated polymers using a colloidal solution of that polymer, said solution having been destabilized. This precipitate, called coacervate, will be adsorbed onto the droplets of the oil emulsion to be coated. By way of example, the document WO 00/48560 describes the production of microcapsules of a mixture of oils and chlorophyll extract, by coacervation, of an aqueous solution of an alcohol having 2 to 4 carbon atoms.

Another encapsulation method based on polymer implementation is polycondensation. This method relies on the polycondensation of two monomers, one of them being compatible with the encapsulation medium, and the other being compatible with the substance to be encapsulated, i.e. the oil. The document U.S. Pat. No. 3,754,062 describes the encapsulation of fats by dissolving a urethane polymer and epichlorhydrin in a fatty liquid, the dispersion of the resulting mixture in the form of droplets in a solution containing a polyamine, and finally the mixture's interfacial polymerization. Castor oil is cited as a product that may be encapsulated using this technique.

Finally, a third method of encapsulation based on the use of polymers is that which implements carboxylated polymers based on a monomer which is (meth)acrylic acid and another monomer which is an acrylic ester (in the literature, these polymers are often designated by the term ASE, which stands for "alkali soluble emulsion"). In this situation, the encapsulation phenomenon is solely governed by the solubility of said polymer depending on the pH. Such polymers are commercially available under the names Eudragit™, Kollicoat™, and Eastacryl 30D™. The encapsulation method in this case consists of mixing said active ingredient in an aqueous solution in the presence of said polymer, then drying the mixture. However, as the examples of this Application demonstrate, these ASE polymers do not make it possible to encapsulate oils.

Continuing their research into encapsulating an oil, this oil being intended to be added to an aqueous formulation, and thereby contributing to the state of the art by means of an alternative solution to those disclosed in the prior art, the Applicant has developed a method for manufacturing an aqueous formulation containing at least one oil, and characterized in that it comprises the steps of:
  a) mixing at least one associative polymer made up of:
     - at least one monomer which is (meth)acrylic acid,
     - at least one monomer which is a (meth)acrylic ester,
     - and at least one associative hydrophobic monomer, with at least one oil and water, in proportions such that the oil represents at least 4% of the total weight of the mixture,
  b) adjusting the pH of the mixture obtained in step a) to a value greater than 6, preferentially 7, very preferentially 8,
  c) potentially precipitating the mixture obtained after step b) by adjusting the pH to a value less than 6, in view of obtaining a dispersion in water of the constituent particles of said polymer and of said oil,
  d) potentially isolating the constituent particles of said polymer and of said oil obtained after step c) by removing the water.

One of the novel elements of the inventive method is using the associative polymers as described in step a) of the aforementioned method. When these polymers are neutralized to a sufficiently high pH (greater than 6, preferentially 7, a very preferentially 8), associative interactions are created between the hydrophobic groups: these interactions mark off the domains which act as solvation cages for the oil molecules. These polymers are often described in the literature using the acronym HASE, which stands for "hydrophobically modified alkali-soluble emulsions".

One of the Applicant's merits is having identified and used the phenomenon of water structuration via such polymers: the oils incorporated into the aqueous formulation are thereby naturally protected. The Applicant emphasizes that the mechanism differs from the mode of encapsulation using ASE polymers, for which the encapsulation phenomenon is solely governed by the solubility of said polymer depending on the pH, as already indicated in the present Application.

Such a use of HASE emulsions is, to our current knowledge, a new use of those objects which have been well-described in painting applications (see documents FR 2,693,203, FR 2,872,815 and FR 2,633,930), and in the concrete sector (see the French patent application with filing number FR 07 00086, not yet published as of the present filing).

Furthermore, the Applicant is also aware of the French patent application, not yet published as of the present filing, which has filing number FR 07 03890. That document describes the implementation of HASE polymers, in view of encapsulating odorizing active ingredients (according to test #5b, the only test which discloses the encapsulation of an odorizing active ingredient which is a cananga oil). This test mentions that said oil is present at a concentration of 3.33% by weight in relation to the total weight of the formulation in which it is incorporated: this is a critical element distinguishing it from the present invention, which only covers formulations containing at least 4% oil by weight in relation to their total weight. Making it possible to encapsulate oil molecules in much higher quantities is also one of the technical advantages offered by the present invention: the percentage of oil by weight may be greater than 10%, 40%, and in some cases, even 60% of the total weight of the aqueous formulation in question.

Consequently, after having carried out steps a) and b) of the inventive method, a mixture is obtained in which the oil molecules are trapped in solvation cages.

In a first variant of the inventive method, a step c) of acidification of the mixture obtained after step b) may also be implemented. This reduction in pH triggers a collapse of the polymer structure: one thus achieves a dispersion in water of solid particles consisting of the polymer and the oil molecules. These oil molecules remain trapped.

In a second variant, one can simultaneously implement stage c) but also a consecutive stage d), which consists of isolating the particles obtained after stage c), by eliminating the water.

Thus, a further advantage of the inventive method is to deliver an aqueous formulation containing a percentage of oil by weight that may sometimes be very high (particularly greater than 60% of the total weight of said formulation) in a form which traps the oil molecules, this form possibly being triple:

that of a liquid which is an aqueous emulsion, whenever the product is prepared by only carrying out the steps a) of mixing and then b) of adjusting the pH to a value greater than 6, that of a liquid, which is a dispersion of particles of said polymer and said oil in water, when the preparation of the product further implements the step of precipitation c) at a pH less than 6, that of solid particles made up of oil molecules trapped by the polymer molecules, when the inventive method's step d) of isolation is implemented.

The Applicant indicates that the unity of the invention between these three embodiments of the invention is ensured by the implementation, in each of these forms, of the HASE polymer (a copolymer of (meth)acrylic acid, an ester of these acids, and an associative hydrophobic monomer). Another one of the Applicant's merits is that she has been able to use the particular behavior of this HASE polymer with regard to the pH, in order to obtain these 3 embodiments of the invention, which give the formulator a great deal of flexibility and freedom.

Finally, a final advantage of the invention is that it may be implemented to trap a large number of oil molecules, regardless of their origin. This is because the person skilled in the art has access to a very large library of associative monomers which he can draw from to identify the monomer that shows the best possible affinity with the oil to be trapped.

A first object of the invention is a method for manufacturing an aqueous formulation containing a at least one oil, and characterized by the fact that it comprises the steps of:

a) mixing at least one associative polymer made up of:
at least one monomer which is (meth)acrylic acid,
at least one monomer which is a (meth)acrylic ester,
and at least one associative hydrophobic monomer,
with at least one oil and water, in proportions such that the oil represents at least 4% of the total weight of the mixture, b) adjusting the pH of the mixture obtained in step a) to a value greater than 6, preferentially 7, very preferentially 8, c) potentially precipitating the mixture obtained after step b) by adjusting the pH to a value less than 6, in view of obtaining a dispersion in water of the constituent particles of said polymer and of said oil, d) potentially isolating the constituent particles of said polymer and of said oil obtained after step c) by removing the water.

In a first variant, the inventive method solely implements the steps a) and b).

In a second variant, the inventive method solely implements the steps a), b), and c).

In a third variant, the inventive method solely implements the steps a), b), c), and d).

The inventive method is further characterized in that during step a), 0.1% to 20%, preferentially 0.1% to 10%, and very preferentially 0.1% to 5% by dry weight of said associative polymer, in relation to the total weight of the mixture obtained after step a), is implemented.

The inventive method is further characterized in that during step a), at least 4%, preferentially at least 10%, very preferentially at least 40%, and extremely preferentially at least 60% by weight of at least one oil, and no more than 70% by weight of at least one oil, in relation to the total weight of the mixture obtained after step a), is implemented.

The inventive method is further characterized in that the pH of the mixture, during step b), is adjusted by means of an organic or mineral base. In practice, the components (the oil, water, associative polymer, and the mineral or organic base) are added during agitation in a reactor; the order in which they are added will be chosen by the person skilled in the art, particularly based on the water-solubility of the oil to be encapsulated.

The inventive method is further characterized in that a strong or somewhat strong acid is implemented during step c).

The inventive method is further characterized in that the monomer, which is a (meth)acrylic ester, is preferentially chosen from ethyl acrylate, butyl acrylate, methyl methacrylate, and mixtures thereof.

The inventive method is further characterized in that said associative hydrophobic monomer possesses the general formula (I):

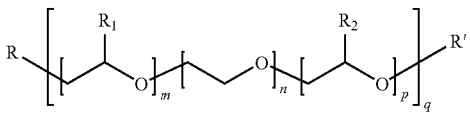

where:
  m, n, p and q are whole numbers and m, n, p are less than 150, q is greater than 0, and at least one whole numbers among m, n and p is nonzero;
  R has a polymerizable vinylic function,
  $R_1$ and $R_2$ are identical or different, and represent hydrogen atoms or alkyl groups,
  R' is a hydrophobic group comprising at least 6 and at most 36 carbon atoms, preferentially at least 16 and at most 24 carbon atoms, and very preferentially at least 18 and at most 22 carbon atoms.

Finally, the inventive method is characterized in that the water is removed by evaporation or centrifugation during step d). However, the person skilled in the art will be able to implement any other technique intended to remove the water from the mixture obtained after steps a) and b).

The inventive method is further characterized in that the oil is chosen from among microalgae oils, *Pongamia pinnata* oil, Jatropha oil, palm oil, sunflower oil, canola oil, almond oil, peanut oil, coconut oil, linseed oil, corn oil, olive oil, grapeseed oil, castor oil, sesame oil, mustard oil, walnut oil, soybean oil, whale oil, sperm oil, cod liver oil, neatsfoot oil, beef tallow or fat, pork fat or lard, borago oil, jojoba oil, macadamia oil, St. John's-wort oil, hazelnut oil, musk rose oil, apricot pit oil, wheatgerm oil, evening primrose oil, duck fat, chicken fat, oleic acid, palmitic acid, linoleic acid, stearic acid, and motor oils.

Another object of the invention is constituted by the aqueous formulation containing at least one oil, and obtained by implementing steps a) and b) of the method described above.

This aqueous formulation, containing at least one oil, is characterized in that it contains water, at least one oil, and at least one associative hydrophobic polymer made up of:
  at least one monomer which is (meth)acrylic acid,
  at least one monomer which is a (meth)acrylic ester,
  and at least one associative hydrophobic monomer,
in that it possesses a pH greater than 6, preferentially 7, very preferentially 8, and in that it contains at least 4% by weight of oil in relation to its total weight.

This aqueous formulation is further characterized in that it contains 0.1% to 20%, preferentially 0.1% to 10%, and very preferentially 0.1% to 5% by dry weight of at least one associative hydrophobic polymer, in relation to its total weight.

This aqueous formulation is further characterized in that it contains at least 4%, preferentially at least 10%, very preferentially at least 40%, and extremely preferentially at least 60% by weight of at least one oil, and no more than 70% by weight of at least one oil, in relation to its total weight.

This aqueous formulation is further characterized in that the monomer, which is a (meth)acrylic ester, is preferentially chosen from ethyl acrylate, butyl acrylate, methyl methacrylate, and mixtures thereof.

This aqueous formulation is further characterized in that said associative hydrophobic monomer possesses the general formula (I):

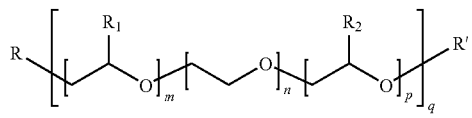

where:
  m, n, p and q are whole numbers and m, n, p are less than 150, q is greater than 0, and at least one whole numbers among m, n and p is nonzero;
  R has a polymerizable vinylic function,
  $R_1$ and $R_2$ are identical or different, and represent hydrogen atoms or alkyl groups,
  R' is a hydrophobic group comprising at least 6 and at most 36 carbon atoms, preferentially at least 16 and at most 24 carbon atoms, and very preferentially at least 18 and at most 22 carbon atoms.

This aqueous formulation is further characterized in that the oil is chosen from among microalgae oils, *Pongamia pinnata* oil, Jatropha oil, palm oil, sunflower oil, canola oil, almond oil, peanut oil, coconut oil, linseed oil, corn oil, olive oil, grapeseed oil, castor oil, sesame oil, mustard oil, walnut oil, soybean oil, whale oil, sperm oil, cod liver oil, neatsfoot oil, beef tallow or fat, pork fat or lard, borago oil, jojoba oil, macadamia oil, St. John's-wort oil, hazelnut oil, musk rose oil, apricot pit oil, wheatgerm oil, evening primrose oil, duck fat, chicken fat, oleic acid, palmitic acid, linoleic acid, stearic acid, and motor oils.

Another object of the invention consists of the formulation made up of solid particles dispersed in water, and obtained by implementing the step of precipitation c) of the method described above.

This dispersion of particles in water is characterized in that said particles contain at least one oil and at least one associative hydrophobic polymer made up of:
  at least one monomer which is (meth)acrylic acid,
  at least one monomer which is a (meth)acrylic ester,
  and at least one associative hydrophobic monomer,
in that it possesses a pH less than 6,
and in that it contains at least 4% by weight of oil, in relation to its total weight.

This dispersion of particles in water is further characterized in that it contains 0.1% to 20%, preferentially 0.1% to 10%, and very preferentially 0.1% to 5% by dry weight of at least one associative hydrophobic polymer, in relation to its total weight.

This dispersion of particles in water is further characterized in that it contains at least 4%, preferentially at least 10%, very preferentially at least 40%, and extremely preferentially at least 60% by weight of at least one oil, and no more than 70% by weight of at least one oil, in relation to its total weight.

This dispersion of particles in water is further characterized in that the monomer, which is a (meth)acrylic ester, is preferentially chosen from ethyl acrylate, butyl acrylate, methyl methacrylate, and mixtures thereof.

This dispersion of particles in water is further characterized in that said associative hydrophobic monomer possesses the general formula (I):

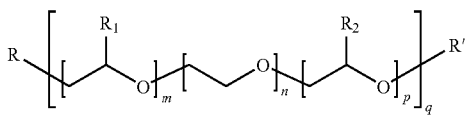

where:
- m, n, p and q are whole numbers and m, n, p are less than 150, q is greater than 0, and at least one whole numbers among m, n and p is nonzero;
- R has a polymerizable vinylic function,
- $R_1$ and $R_2$ are identical or different, and represent hydrogen atoms or alkyl groups,
- R' is a hydrophobic group comprising at least 6 and at most 36 carbon atoms, preferentially at least 16 and at most 24 carbon atoms, and very preferentially at least 18 and at most 22 carbon atoms.

This dispersion of particles in water is further characterized in that the oil is chosen from among microalgae oils, *Pongamia pinnata* oil, Jatropha oil, palm oil, sunflower oil, canola oil, almond oil, peanut oil, coconut oil, linseed oil, corn oil, olive oil, grapeseed oil, castor oil, sesame oil, mustard oil, walnut oil, soybean oil, whale oil, sperm oil, cod liver oil, neatsfoot oil, beef tallow or fat, pork fat or lard, borago oil, jojoba oil, macadamia oil, St. John's-wort oil, hazelnut oil, musk rose oil, apricot pit oil, wheatgerm oil, evening primrose oil, duck fat, chicken fat, oleic acid, palmitic acid, linoleic acid, stearic acid, and motor oils.

Another object of the invention resides in the formulation made up of solid particles obtained by implementing the isolation step d) of the method described above.

These solid particles are characterized in that they contain at least one oil and at least one associative hydrophobic polymer made up of:
- at least one monomer which is (meth)acrylic acid,
- at least one monomer which is a (meth)acrylic ester,
- and at least one associative hydrophobic monomer.

These solid particles are characterized in that said associative hydrophobic polymer possesses the general formula (I):

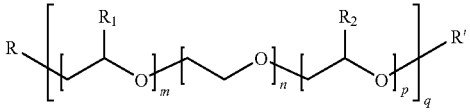

where:
- m, n, p and q are whole numbers and m, n, p are less than 150, q is greater than 0, and at least one whole numbers among m, n and p is nonzero;
- R has a polymerizable vinylic function,
- $R_1$ and $R_2$ are identical or different, and represent hydrogen atoms or alkyl groups,
- R' is a hydrophobic group comprising at least 6 and at most 36 carbon atoms, preferentially at least 16 and at most 24 carbon atoms, and very preferentially at least 18 and at most 22 carbon atoms.

These solid particles are further characterized in that the oil is chosen from among microalgae oils, *Pongamia pinnata* oil, Jatropha oil, palm oil, sunflower oil, canola oil, almond oil, peanut oil, coconut oil, linseed oil, corn oil, olive oil, grapeseed oil, castor oil, sesame oil, mustard oil, walnut oil, soybean oil, whale oil, sperm oil, cod liver oil, neatsfoot oil, beef tallow or fat, pork fat or lard, borago oil, jojoba oil, macadamia oil, St. John's-wort oil, hazelnut oil, musk rose oil, apricot pit oil, wheatgerm oil, evening primrose oil, duck fat, chicken fat, oleic acid, palmitic acid, linoleic acid, stearic acid, and motor oils.

A final object of the invention is the use of aqueous formulations containing at least one oil, of aqueous dispersions of solid particles containing at least one oil, and solid particles containing at least one oil, in the fields of cosmetics, paint, construction, fuels, lubricants, anti-foaming agents, metallurgy, fertilizers, pharmaceuticals, agro chemistry, plant health, detergents, food, leather, and coating.

EXAMPLES

Examples 1 and 2 respectively illustrate the manufacturing of monomers that may be implemented according to the invention, as well as the manufacturing of water-soluble associative polymers that may be implemented according to the invention.

Example 1

Synthesizing Monomers Implemented According to the Invention

Protocol a: Synthesizing Methacrylic Monomers

In a 1-litre reactor, the following is weighed out:
- 400 grams of condensed behenic alcohol with 25 moles of molten ethylene oxide,
- 0.0994 grams of alloocimene,
- 43.75 grams of methacrylic anhydride.

The mixture is heated to 82° C.±2° C. and cooking continues for 3 hours at this temperature. The resulting macromonomer is then diluted with 396 g of methacrylic acid in order to obtain a solution that is liquid at ambient temperature.

Protocol b: Synthesizing Urethane Monomers

In a first step, a precondensate is produced by weighing out in an Ehrlenmeyer flask:
- 13.726 grams of toluene di-isocyanate,
- 36.1 grams of ethyl acrylate,
- 0.077 grams of alloocimene,
- 0.198 grams of dibutyl tin dilaurate.

Next, in a dropping funnel, 10.257 grams of ethylene glycol methacrylate and 10 grams of ethyl acrylate are weighed out. The contents of this funnel are poured into the Ehrlenmeyer flask in 20 minutes at a temperature below 35° C., and it is allowed to react for 30 minutes.

In a second step, the condensation is produced by weighing 132 grams of condensed tri-styryl phenol with 25 moles of ethylene oxide into a 1000 mL reactor, which will be kept molten at 65° C. Next, the precondensate is poured in 20 minutes at 65° C. onto this alcohol, then cooked for 2 hours at 65° C. Finally, the mixture is diluted with 15.5 grams of ethyl acrylate and 84.6 grams of bipermulated water in order to obtain a liquid at room temperature.

Protocol c: Synthesizing Hemimaleate Monomers

In a 1-litre reactor, the following is weighed out:
- 400 grams of branched 32 carbon atom alcohol, condensed with 15 moles of molten ethylene oxide,
- 0.0994 grams of alloocimene,
- 25.3 grams of maleic anhydride.

The mixture is heated to 82° C.±2° C. and cooking continues for 3 hours. The resulting macromonomer is then diluted with 425 g of methacrylic acid in order to obtain a solution that is liquid at room temperature.

Example 2

Synthesizing Associative Water-Soluble Polymers

Protocol A

In a 1-liter reactor, 280 grams of bipermutated water and 3.89 grams of sodium dodecyl sulfate are weighed out. It is heated in the starter to 82° C.±2° C. During this time, a pre-emulsion is prepared, weighing into a beaker:
- 112.4 grams of bipermutated water,
- 2.1 grams of sodium dodecyl sulfate,
- 80.6 grams of methacrylic acid,
- 146.1 grams of ethyl acrylate,
- 55.6 grams of a macromonomer solution as described in protocol a).

Next, 0.85 grams of ammonium persulfate diluted into 10 grams of bipermutated water are weighed out for the first catalyst, and 0.085 grams of sodium metabisulfite diluted in 10 grams of bipermutated water are weighed out for the second catalyst. When the starter is at the right temperature, the two catalysts are added, and polymerization is performed for 2 hours at 76° C.±2° C., adding the pre-emulsion at the same time. The pump is rinsed with 20 grams of bipermutated water and cooked for 1 hour at 76° C.±2° C. Finally, it is cooled to ambient temperature and the resulting polymer is filtered.

Protocol B

In a 1-liter reactor, 280 grams of bipermutated water and 3.89 grams of sodium dodecyl sulfate are weighed out. It is heated in the starter to 82° C.±2° C.

During this time, a pre-emulsion is prepared, weighing into a beaker:
- 334 grams of bipermutated water,
- 3.89 grams of sodium dodecyl sulfate,
- 0.92 grams of dodecyl mercaptan,
- 80.6 grams of methacrylic acid,
- 160.55 grams of ethyl acrylate,
- 60.4 grams of the methacrylurethane solution described in protocol b).

Next, 0.33 grams of ammonium persulfate diluted in 10 grams of bipermutated water are weighed out for the first catalyst, and 0.28 grams of sodium metabisulfite diluted in 10 grams of bipermutated water are weighed out for the second catalyst. When the starter is at the right temperature, the two catalysts are added, and polymerization is performed for 2 hours at 84° C.±2° C., adding the pre-emulsion at the same time. The pump is rinsed with 20 grams of bipermutated water and it is cooked for 1 hour at 84° C.±2° C. Finally, it is cooled to room temperature and filtered.

Protocol C

This protocol is identical to protocol B, except that here, the dodecyl mercaptan is removed in the first step of weighing.

Protocol D

This protocol is identical to protocol A, except that 0.9 grams of dodecyl mercaptan are added in the initial step of weighing in the beaker.

Example 3

This example illustrates the inventive method, in which the steps a) of mixing, b) increasing the pH, and c) reducing the pH are implemented. In particular, it demonstrates that the encapsulation takes place when the associative interactions of the hydrophobic groups of the inventive polymer develop, these interactions being controlled by the specific variations in the pH which the Applicant was able to use to encapsulate an oil. This example illustrates the implementation of the various polymers for encapsulating an oil, which is a sunflower oil.

Test No. 1

This test illustrates a test outside of the invention.

It begins by weighing out 16.5 grams of a polymer made up of 36.9% by weight of methacrylic acid and 63.1% by weight of ethyl acrylate, in the form of a dispersion containing 30% by dry weight of said polymer, 182 grams of water, and 150 grams of a sunflower oil for food distributed by the company ORGELEC™. The pH is then equal to 2.

This polymer is a polymer well-known to the person skilled in the art as the ASE thickening agent whose encapsulation mode has already been described for active ingredients. However, here, after the simple mixing described above, it is observed that 2 phases are obtained: one oil, and the other aqueous containing the polymer.

Next, the pH was gradually increased by successfully adding sodium hydroxide, in intervals of 0.5 pH units, until a final value equal to 9 was reached.

However, after the pH was stabilized at each of these intermediate values, a two-phase system was still observed.

Next, from the pH value equal to 9, the pH was reduced in successive intervals of their 0.5 pH units by successively adding phosphoric acid, until a final value equal to 5 was reached.

However, after the pH was stabilized at each of these intermediate values, a two-phase system was still observed.

This therefore demonstrates well that the ASE polymers do not make it possible to encapsulate oils.

Tests #2 to #12

These tests illustrate the invention.

They begin by weighing 16.5 g of polymer in the form of a dispersion containing 30% by dry weight of said polymer, 182 g of water, and 150 g of a sunflower oil for food distributed by the company ORGELEC™.

In accordance with step a), mixing is carried out.

In accordance with step b), the pH is increased to a value equal to 8 by adding sodium hydroxide.

In accordance with step c), the pH is then reduced to a value equal to 5.9.

The composition of polymers is in table 1.

A dispersion in water of particles made up of oil and the polymer is obtained: the implemented polymers therefore make it possible to effectively encapsulate the sunflower oil.

The size of these dispersions was determined by dynamic light scattering using a Zetasizer™ nano S90 sold by the company MALVERN™.

The storage-stability of these dispersions was also determined by a simple visual observation. It is assumed that they are no longer stable when the homogeneity of the dispersion is lost (the phenomena of sedimentation or surface creaming). These results are given in Table 2.

TABLE 1

| Test # | x | Y | z | $R_1$ | $R_2$ | R | R' | m | n | p | q |
|---|---|---|---|---|---|---|---|---|---|---|---|
| 2 | 37.4 | 54.3 | 8.3 | — | — | methacrylate | branched alkyl with 16 carbon atoms | 0 | 25 | 0 | 1 |
| 3 | 36.7 | 53.1 | 10.2 | — | — | methacrylate | linear alkyl with 22 carbon atoms | 0 | 25 | 0 | 1 |
| 4 | 36.7 | 53.1 | 10.2 | $CH_3$ | — | methacrylate | linear alkyl with 22 carbon atoms | 5 | 25 | 0 | 1 |
| 5 | 36.0 | 53.7 | 10.3 | — | — | methacrylate | branched alkyl with 20 carbon atoms | 0 | 30 | 0 | 1 |
| 6 | 36.0 | 53.7 | 10.3 | — | — | methacrylate | linear alkyl with 18 carbon atoms | 0 | 20 | 0 | 1 |
| 7 | 37.4 | 54.3 | 8.3 | — | — | methacrylate | TSP | 0 | 40 | 0 | 1 |
| 8 | 40.3 | 54.7 | 5.0 | — | — | methacryl urethane | nonylphenol | 0 | 50 | 0 | 1 |
| 9 | 34.6 | 57.7 | 7.7 | — | — | methacrylate | branched alkyl with 28 carbon atoms | 0 | 25 | 0 | 1 |
| 10 | 36.5 | 54.1 | 9.4 | — | — | methacryl urethane | urethane with 12 carbon atoms | 0 | 25 | 0 | 1 |
| 11 | 37.3 | 54.8 | 7.9 | — | — | methacrylate | branched alkyl with 32 carbon atoms | 0 | 25 | 0 | 1 |
| 12 | 37.3 | 54.8 | 7.9 | — | — | methacrylate | branched alkyl with 32 carbon atoms | 0 | 40 | 0 | 1 |

TSP: tristyrylphenol (30 carbon atoms)

With the abbreviations defined in the formula (I), x y and z respectively designating the mass ratios of (meth)acrylic acid, (meth)acrylic esters, and the monomer with formula (I)

TABLE 2

| Test no. | Diameter (nm) | Storage (days) |
|---|---|---|
| 2 | 4030 | 40 |
| 3 | 4680 | >92 |
| 4 | 4300 | 85 |
| 5 | 1950 | >95 |
| 6 | 3780 | 65 |
| 7 | 3530 | 65 |
| 8 | 460 | 27 |
| 9 | 3280 | 65 |
| 10 | 460 | 7 |
| 11 | 3470 | 12 |
| 12 | 3850 | 18 |

Here, the increased effectiveness of the polymers implemented for tests 3, 4 and 5 is particularly observed.

Example 4

This example illustrates the inventive method, in which the steps a) of mixing, b) increasing the pH, and c) reducing the pH are implemented. Here, the tester works with sunflower oil and with the polymer tested according to test #2.

Test No. 13

The test begins by weighing 16.5 g of polymer in the form of a dispersion containing 30% by dry weight of said polymer, 162 g of water, and 200 g of a sunflower oil for food distributed by the company ORGELEC™.

In accordance with step a), mixing is carried out.

In accordance with step b), the pH is increased to a value equal to 8 by adding sodium hydroxide.

In accordance with step c), the pH is then reduced to a value equal to 5.8.

Test No. 14

The test begins by weighing 16.5 g of polymer in the form of a dispersion containing 30% by dry weight of said polymer, 162 g of water, and 250 g of a sunflower oil for food distributed by the company ORGELEC™.

In accordance with step a), mixing is carried out.

In accordance with step b), the pH is increased to a value equal to 8.1 by adding sodium hydroxide.

In accordance with step c), the pH is then reduced to a value equal to 5.8.

Test No. 15

The test begins by weighing 16.5 g of polymer in the form of a dispersion containing 30% by dry weight of said polymer, 162 g of water, and 300 g of a sunflower oil for food distributed by the company ORGELEC™.

In accordance with step a), mixing is carried out.

In accordance with step b), the pH is increased to a value equal to 8.1 by adding sodium hydroxide.

In accordance with step c), the pH is then reduced to a value equal to 5.8.

Test No. 16

The test begins by weighing 16.5 g of polymer in the form of a dispersion containing 30% by dry weight of said polymer, 162 g of water, and 350 g of a sunflower oil for food distributed by the company ORGELEC™.

In accordance with step a), mixing is carried out.

In accordance with step b), the pH is increased to a value equal to 8.1 by adding sodium hydroxide.

In accordance with step c), the pH is then reduced to a value equal to 5.8.

A dispersion in water of particles made up of oil and the polymer is obtained: the implemented polymer therefore makes it possible to effectively encapsulate the oils. The size of these dispersions was determined by dynamic light scattering using a Zetasizer™ nano S90 sold by the company MALVERN™. The results are given in table 3.

TABLE 3

| Test no. | Diameter (nm) |
|---|---|
| 13 | 4240 |
| 14 | 4360 |
| 15 | 4360 |
| 16 | 4620 |

Example 5

This example illustrates the inventive method, in which the steps a) of mixing, b) increasing the pH, and c) reducing the pH are implemented.

Here, the tester works with different oils and polymers.

Tests #17 to #19 implement a polymer made up of 26.3% by weight of ethyl acrylate, 26.3% of methyl methacrylate, 38.2% of methacrylic acid, and 9.2% of a monomer whose formula is (I) in which:

R designates the methacrylate group.
m=p=0 n=25 q=1
R' designates the linear alkyl radical with 22 carbon atoms.

Test No. 17

The test begins by weighing out 33 grams of polymer in the form of a dispersion containing 30% by dry weight of said polymer, 150 grams of water, and 41.6 grams of citronella.

In accordance with step a), mixing is carried out.

In accordance with step b), the pH is increased to a value equal to 8.9 by adding sodium hydroxide.

In accordance with step c), the pH is then reduced to a value equal to 5.8.

Test No. 18

The test begins by weighing out 33 grams of polymer in the form of a dispersion containing 30% by dry weight of said polymer, 150 grams of water, and 26.2 grams of citronella.

In accordance with step a), mixing is carried out.

In accordance with step b), the pH is increased to a value equal to 8.2 by adding sodium hydroxide.

In accordance with step c), the pH is then reduced to a value equal to 5.7.

Test No. 19

The test begins by weighing out 33 grams of polymer in the form of a dispersion containing 30% by dry weight of said polymer, 150 grams of water, and 12.4 grams of citronella.

In accordance with step a), mixing is carried out.

In accordance with step b), the pH is increased to a value equal to 8.2 by adding sodium hydroxide.

In accordance with step c), the pH is then reduced to a value equal to 5.9.

Test No. 20

This test implements the polymer tested in test #2.

The test begins by weighing out 16.5 grams of polymer in the form of a dispersion containing 30% by dry weight of said polymer, 182 grams of water, and 150 grams of a silicon oil.

In accordance with step a), mixing is carried out.

In accordance with step b), the pH is increased to a value equal to 8.2 by adding sodium hydroxide.

In accordance with step c), the pH is then reduced to a value equal to 5.9.

Test No. 21

This test implements the polymer tested in test #11.

The test begins by weighing out 16.5 grams of polymer in the form of a dispersion containing 30% by dry weight of said polymer, 182 grams of water, and 24 grams of behenic alcohol.

In accordance with step a), mixing is carried out, while heating to 85° C.

In accordance with step b), the pH is increased to a value equal to 8.1 by adding sodium hydroxide.

In accordance with step c), the pH is then reduced to a value equal to 5.9.

Test No. 22

This test implements the polymer tested in tests #17 to #19.

The test begins by weighing out 16.5 grams of polymer in the form of a dispersion containing 30% by dry weight of said polymer, 182 grams of water, and 48 grams of behenic alcohol.

In accordance with step a), mixing is carried out, while heating to 85° C.

In accordance with step b), the pH is increased to a value equal to 8.1 by adding sodium hydroxide.

In accordance with step c), the pH is then reduced to a value equal to 5.9.

Test No. 23

This test implements the polymer tested in test #10.

The test begins by weighing out 4.95 grams of polymer in the form of a dispersion containing 30% by dry weight of said polymer, 45.5 grams of water, and 37.5 grams of tetradodecane.

In accordance with step a), mixing is carried out, while heating to 85° C.

In accordance with step b), the pH is increased to a value equal to 8.1 by adding sodium hydroxide.

In accordance with step c), the pH is then reduced to a value equal to 5.9.

A dispersion in water of particles made up of oil and the polymer is obtained: the implemented polymer therefore makes it possible to effectively encapsulate the oils. The size of these dispersions was determined by dynamic light scattering using a Zetasizer™ nano S90 sold by the company MALVERN™. The results are given in table 4.

TABLE 4

| Test no. | Diameter (nm) |
| --- | --- |
| 17 | 1800 |
| 18 | 650 |
| 19 | 520 |
| 20 | 2060 |
| 21 | 4400 |
| 22 | 5200 |
| 23 | 2200 |

The invention claimed is:

1. A method for producing an aqueous formulation comprising at least one oil, the method comprising:
   a) mixing at least one associative polymer comprising, in polymerized form:
      at least one (meth)acrylic acid monomer;
      at least one (meth)acrylic ester monomer; and
      at least one associative hydrophobic monomer,
   with the at least one oil and water, to get a mixture, in proportions such that the at least one oil is at least 4% based on total weight of the mixture,
   b) adjusting a pH of the mixture in a) to a value greater than 6;
   c) precipitating the mixture after b) by adjusting the pH to a value less than 6, to obtain a dispersion in water of constituent particles of the at least one associative polymer and of the at least one oil; and
   d) optionally, isolating the constituent particles obtained after c) by removing the water.

2. The method according to claim 1, comprising solely a), b), c), and d).

3. The method according to claim 1, wherein, during a), 0.1% to 20%, by dry weight of the at least one associative polymer, in relation to the total weight of the mixture obtained after a), is implemented.

4. The method according to claim 1, wherein at least 4%, and at most 70% by weight of the at least one oil, in relation to the total weight of the mixture obtained after a), is implemented.

5. The method according to claim 1, wherein the pH of the mixture, during b), is adjusted with an organic or mineral base.

6. The method according to claim 1, wherein the pH of the mixture, during c), is adjusted with a strong acid.

7. The method according to claim 1, wherein the (meth) acrylic ester monomer is at least one selected from the group consisting of ethyl acrylate, butyl acrylate, and methyl methacrylate.

8. The method according to claim 1, wherein the at least one associative hydrophobic monomer is represented by formula (I):

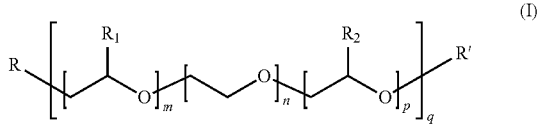

wherein:
m, n, p and q are whole numbers and m, n, p are less than 150, q is 1,
and at least one whole number among m, n and p is nonzero;
R comprises a polymerizable vinylic function;
$R_1$ and $R_2$ are identical or different, and each represents a hydrogen atom or alkyl group; and
R' is a hydrophobic group comprising at least 6 and at most 36 carbon atoms.

9. The method according to claim 1, comprising d), and wherein the water is eliminated by evaporation or centrifugation during d).

10. The method according to claim 1, wherein the at least one oil is selected from the group consisting of a microalgae oil, *Pongamia pinnata* oil, Jatropha oil, palm oil, sunflower oil, canola oil, almond oil, peanut oil, coconut oil, linseed oil, corn oil, olive oil, grapeseed oil, castor oil, sesame oil, mustard oil, walnut oil, soybean oil, whale oil, sperm oil, cod liver oil, neatsfoot oil, beef tallow or fat, pork fat or lard, borago oil, jojoba oil, macadamia oil, St. John's-wort oil, hazelnut oil, musk rose oil, apricot pit oil, wheatgerm oil, evening primrose oil, duck fat, chicken fat, oleic acid, palmitic acid, linoleic acid, stearic acid, and a motor oil.

11. A dispersion of at least one particle in water, wherein said at least one particle comprises:
at least one oil; and
at least one associative hydrophobic polymer comprising, in polymerized form:
at least one (meth)acrylic acid monomer;
at least one (meth)acrylic ester monomer; and
at least one associative hydrophobic monomer, and
wherein the dispersion has a pH less than 6,
and comprises at least 4% by weight of the at least one oil, in relation to its total weight.

12. The dispersion of at least one particle in water according to claim 11, comprising 0.1% to 20% by dry weight of the at least one associative hydrophobic polymer, in relation to total weight of the dispersion.

13. The dispersion of at least one particle in water according to claim 11, comprising at least 4%, and no more than 70% by weight of the at least one oil, in relation to total weight of the dispersion.

14. The dispersion of at least one particle in water according to claim 11, wherein the (meth)acrylic ester monomer is at least one selected from the group consisting of ethyl acrylate, butyl acrylate, and methyl methacrylate.

15. The dispersion of at least one particle in water according to claim 11, wherein the at least one associative hydrophobic monomer is represented by formula (I):

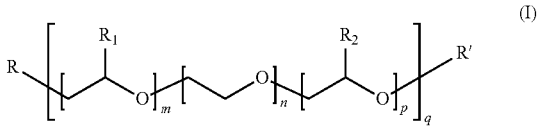

wherein:
m, n, p and q are whole numbers, m, n, p are each from zero to less than 150, q is 1, and at least one among m, n and p is nonzero;
R comprises a polymerizable vinylic function;
$R_1$ and $R_2$ are identical or different, and each represents a hydrogen atom or alkyl group;
R' is a hydrophobic group comprising at least 6 and at most 36 carbon atoms.

16. The dispersion of at least one particle in water according to claim 11 wherein the at least one oil is at least one selected from the group consisting of a microalgae oil, *Pongamia pinnata* oil, Jatropha oil, palm oil, sunflower oil, canola oil, almond oil, peanut oil, coconut oil, linseed oil, corn oil, olive oil, grapeseed oil, castor oil, sesame oil, mustard oil, walnut oil, soybean oil, whale oil, sperm oil, cod liver oil, neatsfoot oil, beef tallow or fat, pork fat or lard, borago oil, jojoba oil, macadamia oil, St. John's-wort oil, hazelnut oil, musk rose oil, apricot pit oil, wheatgerm oil, evening primrose oil, duck fat, chicken fat, oleic acid, palmitic acid, linoleic acid, stearic acid, and a motor oil.

* * * * *